United States Patent [19]

Fischer et al.

[11] Patent Number: 4,556,056

[45] Date of Patent: Dec. 3, 1985

[54] TRANSPARENT FLUID BANDAGE MATERIAL AND THE PREPARATION AND USE THEREOF

[75] Inventors: Herbert Fischer, Burg; Botho Kickhöfen, Freiburg; Eckehard Vaubel, Berlin, all of Fed. Rep. of Germany

[73] Assignee: Max-Planck-Gesellschaft zur Forderung der/Wissenschaften e.V., Gottingen, Fed. Rep. of Germany

[21] Appl. No.: 501,056

[22] Filed: Jun. 9, 1983

Related U.S. Application Data

[63] Continuation of Ser. No. 284,266, Jul. 17, 1981, abandoned, which is a continuation of Ser. No. 74,613, Sep. 12, 1979, abandoned, which is a continuation-in-part of Ser. No. 880,524, Feb. 23, 1978, abandoned.

[30] Foreign Application Priority Data

Jun. 3, 1977 [DE] Fed. Rep. of Germany ....... 2725261

[51] Int. Cl.[4] ............................................. A61L 15/00
[52] U.S. Cl. .................................... 128/156; 128/155
[58] Field of Search ............... 3/1; 604/368, 369, 371, 604/374, 291, 890, 892; 128/155, 156, 403

[56] References Cited

U.S. PATENT DOCUMENTS

| 3,742,951 | 7/1973 | Zaffaroni | 424/28 |
|---|---|---|---|
| 3,812,252 | 5/1974 | Silvetti | 424/DIG. 13 |
| 3,871,376 | 3/1975 | Kozak | 604/291 |
| 3,901,236 | 8/1975 | Assarsson et al. | 604/368 |
| 3,935,308 | 1/1976 | Wise et al. | 424/DIG. 13 |
| 3,941,858 | 3/1976 | Shepherd et al. | 3/1 |
| 3,961,379 | 6/1976 | Highgate | 3/1 |
| 3,963,685 | 6/1976 | Abrahams | 128/155 |
| 3,980,084 | 9/1976 | Kross | 128/283 |
| 3,997,660 | 12/1976 | Kopececk et al. | 424/DIG. 13 |
| 4,028,290 | 6/1977 | Reid | 524/768 |
| 4,045,547 | 8/1977 | Le Boeuf et al. | 424/28 |
| 4,076,663 | 2/1978 | Mosuda et al. | 604/368 |
| 4,086,331 | 4/1978 | Neumann et al. | 424/DIG. 13 |
| 4,156,067 | 5/1979 | Gould | 128/156 |
| 4,192,727 | 3/1980 | Ward | 128/156 |

*Primary Examiner*—Ben R. Padgett
*Assistant Examiner*—T. J. Wallen
*Attorney, Agent, or Firm*—Bernard, Rothwell & Brown

[57] ABSTRACT

Novel bandage materials are provided comprising a transparent fluid material consisting of hydrophilic organic transparent gel in sheet or band form, swollen with an aqueous solution which can contain buffer substances, wound treatment agents, nutrients and/or hormones, and optionally, a reinforcing mesh. The fluid bandages are made by dissolving a monomer and a gellable hydrophilic high molecular substance in aqueous medium and starting the gel forming reaction with an initiator for the polymerizable monomer. The bandages can also be utilized as carrier compositions for cell cultures from which metabolites are obtained.

44 Claims, No Drawings

TRANSPARENT FLUID BANDAGE MATERIAL AND THE PREPARATION AND USE THEREOF

This application is a continuation of application Ser. No. 284,266 now abandoned, filed July 17, 1981, which is a continuation of Ser. No. 074,613 filed Sept. 12, 1979 now abandoned, which is in turn a continuation-in-part of Ser. No. 880,524 filed Feb. 23, 1978, now abandoned.

The invention relates to a transparent, fluid bandage material, especially for the treatment of wounds. In additional aspects, the invention relates to a method of preparing the bandage material, and to methods of use thereof.

The bandaging art, in the case of wounds which heal poorly, burns, ulcerations, etc., has been directed hitherto almost entirely toward the development of bandage materials which will conform to the wound area and which can easily, painlessly and bloodlessly be removed for replacement.

These bandage materials consist of lubricant-impregnated textiles, sometimes of synthetic fabrics, and sometimes also of cotton. In further development, a variety of substances were then added to these materials, such as disinfectants or antibiotics, for example. The disadvantage of these materials, however, is that, in the case of heavily suppurating wounds, a bandage material is being applied which is highly moisture-repellent. The lubricant in the fabric permits the easy removal of the bandage, but it seals the wound relatively air-tight with a lubricant film, so that fluid retention can be produced in heavily oozing wound areas.

Another method of treatment involves the application of moist bandages. This is accomplished either by spraying the wounds, which are covered by muslin pads, with a variety of substances or, especially in dermatology, by the use of occlusive bandages.

However, these bandages are subject to two important disadvantages. In the case of occlusive bandages (consisting usually of a moisture-impregnated compress covered by a film), dermal maceration takes place. In moist bandage treatment, the constant spraying produces a relatively great chill due to evaporation; beds are very hard to keep dry, and consequently greater care problems are created, quite aside from the relatively high cost of the substances being sprayed on, which have to be used in large amounts.

Weeping and granulating wounds should be treated with absorbent materials which can be removed relatively easily and which should be transparent to permit detection of any superinfections.

The covering and treatment of large-area wounds and ulcerations has been accomplished hitherto by means of opaque membranes, salves, foams or bandage materials. The visual observation of the healing process and the detection of complications has therefore been impossible. Furthermore, the bandage materials often stick fast to the wound so that changing the bandages results in bleeding and interfered with healing. Cicatricial keloids have therefore often been the late consequencs of such treatment.

Also known is a synthetic skin substitute for bandaging purposes, consisting of a porous, soft polyurethane foam layer and an outside covering of microporous polytetrafluorethylene film. This material is opaque and therefore has the above-stated disadvantages associated with opacity. Furthermore, this material is designed to adhere to the wound, so that, when it is removed, the granulations come off with it. The bandage must therefore be changed at brief intervals.

Further, a bandage material which consists of a liquid solvent, namely polyethylene glycol, and a poly-(2-hydroxyethylmethacrylate) in powder form is convention in the art. This material is applied by putting drops of the liquid solvent to the wound and spreading them around, and then sprinkling the polymer powder over it. With this material, its production in situ on the wound is essential, the use of a liquid premixture having proven to be unfeasible. All in all, it is not a bandage material at all, but something intermediate between a salve and a wound covering film applied in liquid form, which likewise has the disadvantages described above.

The invention substantially overcomes or mitigates these problems by providing a hydrophilic, fluid bandage material, which is transparent and therefore permits the observation of the skin areas beneath it. The bandage material of the invention also permits bandage changing without bleeding or other interferences with the healing process, and furthermore permits the simultaneous application of substances important for the treatment and healing of the wound, without having the disadvantages formerly encountered in moist bandages.

German Patent Specification No. 27 25 261.5 describes a transparent, liquid dressing material which is especially suitable for the treatment of wounds, but also for the after-treatment of skin tumors, desensitizing of allergies, cosmetic purposes, keeping moist exposed bones and tendons, psoriasis and as a carrier for cell cultures, which material consists of a hydrophilic, organic, transparent gel in sheet or strip form, which is present swollen with an aqueous solution, which can contain buffer substances, active materials conventional in the treatment of wounds, nutrient materials and/or growth materials, the gel optionally also containing thread- or mesh-like strengthening materials.

A special advantage of this dressing material is that it is particularly easy to use and can be removed or changed without disturbing the healing process, permits the visual observation of the underlying parts of the body or cell cultures, brings about an improved wound healing without excess granuloma formation and permits the application of active materials through the material itself.

However, in the case of storing and keeping a supply of this transparent liquid dressing material, the high liquid content thereof is a disadvantage. Furthermore, the application of active materials and the removal of secreta takes place relatively slowly.

Therefore, it is an object of the present invention to maintain all the advantages of the above-mentioned transparent liquid dressing material, while making it available in a form which is more easily stored and which permits the rapid application of active materials and the rapid removal of secreta.

This problem is solved, according to the present invention, by a transparent dressing material of the above-described kind which is in the form of a dry, clear, swellable film.

The dressing material according to the present invention is a skin-like, glass-clear film which has a great ability to reswell and, even in a short time, i.e., within the course of about 1 hour, can take up to 10 times its weight, or even more, of liquid and subsequently reswells almost completely with the recreation of all of the mechanical and structural properties of the swollen starting material. In general, the weight of the dried film is 2 to 10% and preferably 3 to 7% by weight of the swollen, moist starting material. The thickness of the film is generally from about 0.5 to 0.01 mm and preferably from 0.3 to 0.003 mm, measured without the strengthening material.

The fluid bandage material of the invention, after reswelling has taken place, can be described as a transparent gel sheet material having usually a thickness between 0.5 and 10 mm, preferably between 1 and 5 mm, and containing an aqueous solution. The solution contains, in dissolved form, the substances important to the treatment and healing of the wound, such as buffer substances, antiseptics, antibiotics, medicinal substances, nutrients, hormones, local anaesthetics, and the like. All these substances are known in the treatment of the skin and of wounds, and the expert is familiar with them. It is therefore unnecessary to specify them here in detail.

For physical reinforcement, the fluid bandage material of the invention can obtain a reinforcing material embedded in mesh or string form in the gel, the individual filaments or fibers thereof having to be so disposed as not to impair substantially the transparency of the material. Preferably, the reinforcing material is in the form of a course mesh. The reinforcing material consists of natural or artificial fibers and filaments which are inert with respect to the solution and to the gel itself.

The most important component of the fluid bandage material of the invention is the hydrophilic, transparent, organic gel. This gel consists preferably of a mixture of hydrophilic polymer and at least one gellable substance of high molecular weight. The term, "polymer", as used herein, is to be understood to mean compounds which have been produced synthetically from monomeric units by polymerization, that is by polyaddition or polycondensation. They can be homopolymers or copolymers of two or more different monomeric units. The polymer can also be cross-linked by the incorporation of monomers containing more than one group capable of addition or condensation. It is important, however, that the polymer be so hydrophilic that it is capable of forming a transparent gel in an aqueous medium. For this, it is necessary that the monomeric units contain a sufficient number of hydrophilic groups, such as OH groups, $NH_2$ groups, COOH groups, and the like.

In the preferred embodiment, the gel contains, in addition to the above-defined polymer, at least one gellable, preferably natural, substance of high molecular weight. The gellable carbohydrates and gellable polyamino acids and the combinations and derivatives are especially suitable as such.

The polymer and the gellable substance of high molecular weight can be present together in an ordianry mixture in which the components are freely movable; they can be in the form of a three-dimensional network which consists of cross-linked polymer and in whose pores the molecules of the gellable, high-molecular substance are held as in a cage (this structure is obtained by preparing the polymer with cross-linking in the presence of the high-molecular substance), or the polymer and the high-molecular substance can also be linked together by covalent bonds.

It is especially preferred that the hydrophilic, transparent, organic gel be composed of a polymer of a hydrophilic acrylic acid or methacrylic acid derivative and at least one gellable polysaccharide and/or protein or polypeptide.

We have found that especially favorable drying and reconstituting properties are obtained when the polymerized acrylic or methacrylic acid derivative is present in at least the same amount by weight as the polysaccharide and/or protein and preferably accounts for 60 to 90% by weight of the total gel dry mass.

It is especially preferred to use an amide or an ester with an alkanol as the hydrophilic acrylic acid or methacrylic acid derivative, and in the case of the ester, the alkanol moiety can also contain one or more additional free hydroxyl groups. The alkanol moiety generally contains 1 to 6 carbon atoms. If no free hydroxyl groups are present, alkanols having 1 or 2 carbon atoms are preferred.

Typical examples of this preferred group of monomers for the polymerization components of the gel material are accrylamide, methacrylamide, ethyl acrylate, methyl acrylate, propyl acrylate, butyl acrylate and the corresponding methacrylates, hydroxyethyl acrylate, hydroxypropyl acrylate, hydroxybutyl acrylate, the corresponding methacrylates, acrylic acid glycerine ester, acrylic acid erythritol ester, acrylic acid pentaerythritol ester, and the corresponding methacrylic acid compounds. Bifunctional or polyfunctional polymerizable compounds, such as methylenebisacrylamide and the like, are added as cross-linking agents. These cross-linking agents are known to the expert and therefore no further examples are given thereof.

The gel contains preferably agarose as the gellable polysaccharide. Other suitable polysaccharides, for example, are pectins, starch, dextrans, polyglycols, cellulose derivatives and agar-agar. Gellability is essential to suitability in the scope of the invention, that is transparent, gelatinous masses must be formed. Of the gellable proteins or polypeptides, as the case may be, gelatine is preferred.

The gels are prepared preferably by polymerization of the monomer or monomers which are to serve as the polymer component, in the presence of the high-molecular substance, in an aqueous solution, through the addition of suitable polymerization initiators, such as per compounds, an example being ammonium persulfate, or by the creation of the conditions required for polycondensation.

The artisan is thoroughly familiar with the polymerization conditions and polymerization initiators which are appropriate to the hydrophilic monomers to be used in particular cases, so that a listing thereof can be omitted.

The swollen gel plates obtained in the above-described are preferably dried from both sides. In this case, it is desirable to proceed in such a manner that, as drying progresses, distortion, for example waving, is prevented. According to one embodiment of the process according to the present invention, this is achieved by drying the gel between two porous supporting bodies, such supporting bodies being, for example, porous synthetic resin plates, perforated metal plates or foils or the like. If the porous supporting bodies are used in the form of comparatively thin foils, then they, in turn, are preferably carried by an appropriate supporting construction.

According to another embodiment of the present invention, the wet gel is stretched on the thread- or mesh-like strengthening material and dried in this form. The drying itself can be carried out at ambient temperature or at an elevated temperature, in a vacuum or at atmospheric pressure. In the case of the above-described sandwich technique with drying between two porous supporting bodies, we have ascertained that a vacuum of as low as 1 to 10 mm Hg can be used without the properties of the dried film, with regard to the recovery of the mechanical and structural properties of the wet starting material, thereby being substantially impaired. If drying is carried out without the use of a vacuum, for example in a current of warm air, then, as supporting bodies, it is preferable to use metal plates or foils in order to ensure a better transmission of heat.

Gels with an initial thickness of from about 0.5 to about 3 mm have proved to be especially suitable for the drying process. When using porous supporting bodies, the best results have been obtained with gels with a thickness of from 1 to 2 mm; with increasing thickness within this range, the use of a vacuum gives better results than without the use of a vacuum. If drying is carried out without a vacuum in a current of warm air, then the best results are achieved with a gel thickness of 1 mm or less.

By means of the present invention, substantial improvements are achieved in comparison with the material according to German Patent Specification No. 27 25 261.5. Thus, in the case of the dried dressing film, difficulties in packing do not arise and the maintenance of sterility is also much simpler. On the other hand, the already moisture-saturated gel subsequently takes up active materials, for example, antibiotics, cytostatics, wound hormones, nutrient substances, local anaesthetics and the like, only relatively slowly because of an exchange must take place between the liquid present on the outside and that enclosed in the gel. However, in the case of the dry dressing according to the present invention, this exchange takes place substantially more quickly since the solution containing the active materials is directly sucked up.

Finally, the dressing material according to the present invention in the dry form, even without previous rehydration or in the case of only partial rehydration, is especially good in the case of strongly suppurating wounds since it sucks up secreta to a greater extent than already completely swollen material. In this manner, it is possible to suck up the same amount of secreta as can only be achieved in the case of the dressing material according to German Patent Specification No. 27 25 261.5 by providing flow-off holes in the material.

One especially advantageous and surprising property of the bandage material of the invention is that in the rehydrated or reswollen form, it adheres well to sound tissue, but does not stick to the wound itself. This permits an easy changing of the bandage when necessary.

As a result of the transparency or translucency of the material, the course of the healing process can always be followed visually. Since the gel is in the moist state, it is furthermore possible to apply substances to be used for the treatment and healing of the wound without changing the bandage, simply by applying them to the bandage in place. They then diffuse in dissolved form through the bandage to the skin surface beneath it, and can act thereon. On the other hand, drainage of wounds can be fortified by perforations.

Furthermore, the absorbency and moisture retaining ability of the bandage material can be controlled through the selection of the ratio of the acrylic or methacrylic acid derivative to the gellable polysaccharide or protein.

As stated previously, the bandage material of the invention can already contain dissolved active ingredients. Preferably, however, the substances desired in each case are applied only upon reswelling of the bandage, or thereafter, since there are different methods of treatment, and a gel bandage that has not yet been impregnated with the medication can therefore more easily be adapted to the various methods by after-impregnation. If, for example, a reswollen bandage material of the invention is placed in an iodine-polyvidone solution, a yellowish-orange coloration can be seen within only five minutes, and after ten minutes a considerable part of the iodine has apparently diffused into the material. Water-miscible solvents like dimethylsulfoxide or polyethyleneglyclols can be used as carriers.

The material of the invention remains relatively unaltered on the wound itself, even though the wound be severely purulent, but it dries solid at the margins, so that from there to the edge a good adhesion is obtained.

Preferably, when the bandage material of the invention is used, another bandage consisting of lubricated gauze is placed over it to protect it, since the lubricated gauze bandage is hydrophobic and retains the liquid in the actual bandage material.

In one proven method of application, the bandage material of the invention is laid on the wound so that it can dry solid at the margins, and then a relatively heavily lubricated gauze bandage is laid on it, followed by a thin compress bandage and an elastic bandage.

Clinical tests with the bandage material of the invention have shown that it is absolutely tolerable, can be used in an ideally simple fashion, and can be removed or changed without any difficulty. A special advantage is to be seen in the fact that the healing of the wound under the bandage material takes place more rapidly, without excessive granulation, thereby forestalling the development of cicatricial keloids.

The bandage material of the invention is especially suitable for the healing of wounds, especially burns and chronic ulcerations. Other applications are the management of skin tumors, desensitization of allegrgies, cosmetic surgery, and the like, keeping moist exposed bones and tendons, regeneration of necrosis-endangered structures, such as tendons and exposed fascia, surface anaesthesia and psoriasis, a good observation of the removal of epithelial cells being possible.

In rod form, the dressing material can be used for the treatment of osteomyelitides, preferably with the addition of tauroline or gentamycin. It can also be used as a tamponade in dentistry, for example, in spheroidal form with cast in threads in order to facilitate withdrawal thereof.

The bandage material of the invention can furthermore be used advantageously as a medium for cell cultures.

The following examples will explain the preparation of the bandage material of the invention.

EXAMPLES 1-6

3.5 grams acrylamide and 91 mg N,N'-methylene-bis-acrylamide are dissolved in 50 ml distilled water. 2 grams Agarose or agar-agar are dissolved in 50 ml distilled water at 100° C. in a water bath and then allowed to cool to 60° C., then mixed with 60 $\mu$l N,N,-N',N'-tetramethylene-diamine (TEMED) and 45 mg ammonium peroxydisulphate and subsequently mixed with the acrylamide solution and immediately poured into a polymerization chamber. This is closed with a glass cover in such a manner that no air bubbles are entrapped. The chamber is kept for about 30 minutes at 56° C., until it is certain that the acrylamide has polymerized. After cooling, the plate is left to ripen for at least 24 hours at 4° C. After removal from the polymerization chamber, the gel is washed several times in phosphate-buffered sodium chloride solution, optionally with the addition of sodium azide, methiolate, or one or more other additives, in order to allow nonpolymerized material to diffuse out. If a fabric-reinforced gel is desired, then a fabric, preferably of cotton, is placed in the polymerization chamber before pouring in the polymerization mixture.

Five other gels are prepared in the same manner which differ from one another with regard to the content of polyacrylamide (P) and of agarose (A). The compositions are given in the following Table.

The individual gels are brought to a thickness of 1 to 2 mm and then placed between porous synthetic plates made of polyethylene (produced by Pharmacia, Sweden) and dried at a vacuum of 2 to 5 mm Hg and at ambient temperatures. The following Table also gives the weight of the films obtained as a percentage of the moist weight of the starting material.

Reswelling is carried out by placing in water, the period of time and the degree of reswelling achieved is also given in the following Table:

| P % | 2.5 | 2.5 | 5 | 3.5 | 3.5 | 3.5 |
|---|---|---|---|---|---|---|
| A | 1 | 1 | 1 | 0.5 | 1.5 | 2 |
| dry wt. in % of wet at. | 3.4 | 4.8 | 6.6 | 3.8 | 5.4 | 6.1 |

| time (hrs.) | reswelling to % of the initial weight before drying | | | | | |
|---|---|---|---|---|---|---|
| 1 | 46.7 | 56.5 | 50.3 | 58.5 | 51.1 | 55.5 |
| 6 | 54.2 | 82.9 | 95.6 | 81.0 | 76.5 | 72.2 |
| 24 | 55.7 | 84.9 | 97.1 | 82.3 | 78.6 | 74.1 |

EXAMPLE 7

Polyacrylamide (5%), gelatine (5%)

5 grams Acrylamide and 130 mg N,N'-methylene-bis-acrylamide are dissolved in 50 ml distilled water and the solution heated to 60° C. Furthermore, 5 grams gelatine are dissolved in 50 ml hot distilled water and also kept at 60° C. A glass plate with the dimensions of 12.5×26 cm and with a 2 mm high rim is preheated to 65° C. on a hot plate. The two above-mentioned solutions are mixed hot, 60 μl. N,N,N',N'-tetramethylenediamine (TEMED) and 45 mg ammonium peroxydisulphate are added thereto, mixed up and polymerized, washed and dried in the manner described in Example 1.

EXAMPLE 8

Polyacrylamide (3.5%), Agarose (2%) and Polyethylene Glycol (2%)

3.2 grams Acrylamide and 82 grams N,N'-methylene-bis-acrylamide are dissolved in 30 ml distilled water. Furthermore, two solutions are prepared, each of 1.8 grams agar-agar or agarose and of polyethylene glycol 6000 in 30 ml distilled water. The agarose is dissolved in 100° C. and thereafter all three solutions are kept at 60° C. After mixing, 60 μl TEMED or a mixture of TEMED and 3-dimethylaminopropionitrile, as well as 45 mg ammonium peroxydisulphate, are quickly added thereto. The casting and further working up of the plate obtained are carried out in the manner described in Example 1.

EXAMPLE 9

Polyacrylamide (7.5%), Methyl Cellulose (5%)

7.5 grams Acrylamide and 195 mg N,N'-methylene-bis-acrylamide are dissolved in 50 ml. distilled water and heated to 60° C. A second solution is prepared by dissolving 5 grams methyl cellulose in 50 ml distilled water, taking care that no lumps remain behind and that a homogeneous solution is formed. Both solutions are mixed together at 60° C., the catalysts are added as described in Example 1 and the plate cast and dried in the manner also described in Example 1.

It is also possible to replace the catalysts by riboflavin, in which case, for polymerization, the plate must be exposed to a source of light similar to daylight.

It will be understood that the specification and examples are illustrative, but not limitative of the present invention and that other embodiments within the spirit and scope of the invention will suggest themselves to those skilled in the art.

What is claimed is:

1. Transparent dressing material which is especially useful for the treatment of wounds, comprising a dry, swellable clear film of hydrophilic, organic transparent gel in the form of a sheet or strip and wherein said gel comprises (a) at least one gellable agar-agar, agarose, gelatine or methyl cellulose and (b) a hydrophilic polymer which has been prepared by polymerization of acrylamide or methacrylamide in an aqueous medium containing component (a).

2. Dressing material as claimed in claim 1 additionally containing a nutrient or growth material.

3. Dressing material of claim 1, wherein component (a) is agar-agar.

4. Dressing material of claim 1, wherein component (a) is agarose.

5. Dressing material of claim 1, wherein said hydrophilic polymer is prepared by polymerization of acrylamide.

6. Dressing material of claim 1, wherein the gel comprises 50 to 90 percent by weight of polymerized acrylamide or methacrylamide and 50 to 10 percent by weight of agar-agar, agarose, gelatine or methyl cellulose.

7. Dressing material of claim 1, wherein said hydrophilic polymer is cross-linked.

8. Dressing material of claim 7, wherein said hydrophilic polymer is cross-linked with a bifunctional or polyfunctional polymerizable component.

9. Transparent fluid bandage material comprising a hydrophilic organic transparent gel sheet swollen with an aqueous solution containing buffer substances, wound treatment agents, nutrients and/or hormones and comprising (a) at least one gellable agar/agar, agarose, gelatine or methyl cellulose and (b) a hydrophilic polymer which has been prepared by polymerization of acrylamide or methacrylamide in an aqueous medium containing component (a).

10. Fluid bandage material of claim 9, wherein component (a) is agar-agar.

11. Fluid bandage material of claim 9, wherein component (a) is agarose.

12. Fluid bandage material of claim 9, wherein said hydrophilic polymer is prepared by polymerization of acrylamide.

13. Fluid bandage material of claim 9, wherein the gel comprises 50 to 90 percent by weight of polymerized acrylamide or methacrylamide and to 50 10 percent by weight of agar-agar, agarose, gelatin or methyl cellulose.

14. Fluid bandage material of claim 9, wherein said hydrophilic polymer is cross-linked.

15. Fluid bandage material of claim 14, wherein said hydrophilic polymer is cross-linked with a bifunctional or polyfunctional polymerizable component.

* * * * *